United States Patent [19]

Yeh

[11] Patent Number: 5,116,346
[45] Date of Patent: May 26, 1992

[54] DISPOSABLE DERMAL CURETTE
[75] Inventor: Charles R. Yeh, Plantation, Fla.
[73] Assignee: Acuderm, Inc., Ft. Lauderdale, Fla.
[21] Appl. No.: 697,721
[22] Filed: May 3, 1991

Related U.S. Application Data

[63] Continuation of Ser. No. 427,791, Oct. 27, 1989, abandoned.

[51] Int. Cl.⁵ .................. A61B 17/32; A61B 17/50
[52] U.S. Cl. .................. 606/131; 606/160; 16/110 R; 81/489
[58] Field of Search ............. 606/84, 160, 161, 167, 606/131, 210, 211, 206; 128/757, 758; 81/489; 16/110 R; D8/DIG. 7; 30/164.9

[56] References Cited

U.S. PATENT DOCUMENTS 1,089,019  3/1914  Swasey .................. 606/131 X
3,502,082  3/1970  Chatfield .................. 606/160
4,414,974  11/1983  Dotson et al. .................. 606/167

OTHER PUBLICATIONS

Mueller "The Surgical Armamentarium" 1980, p. 161.

Primary Examiner—Michael H. Thaler
Attorney, Agent, or Firm—Rockey and Rifkin

[57] ABSTRACT

A disposable dermal curette for scraping lesions from the surface of a patient's skin, comprising a generally cylindrical plastic handle having a proximal end portion, a distal end portion, a mid-section portion with a flattened section recessed relative to the proximal end and distal end portions, and a generally circular or loop-shaped working element, with at least one cutting edge, attached to the proximal end portion. The distal end portion is provided with a textured surface and, for maximum control and proper balance, additional textured surfaces may be provided on the mid-section and proximal end portions.

8 Claims, 1 Drawing Sheet

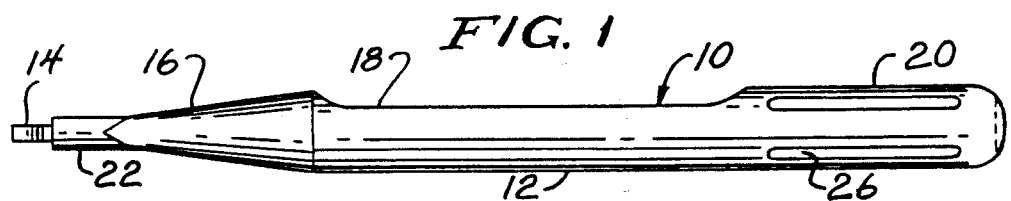
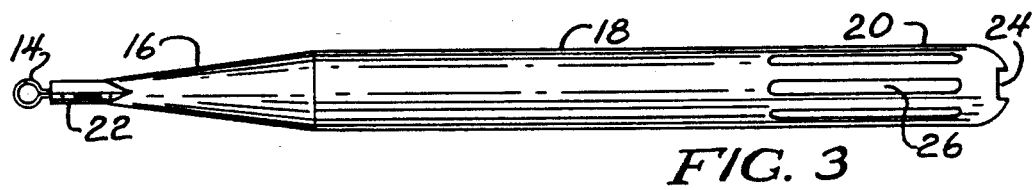
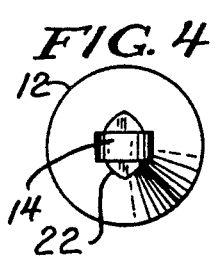
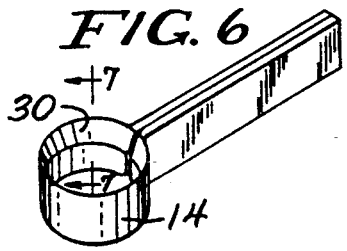
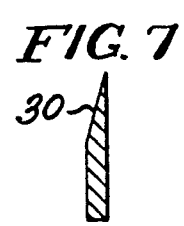
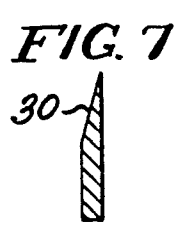
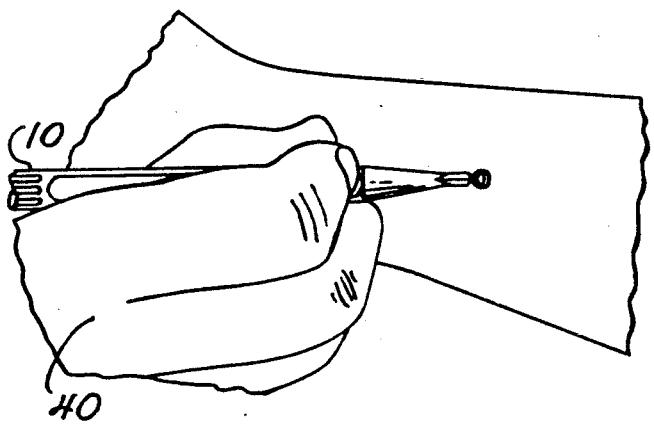
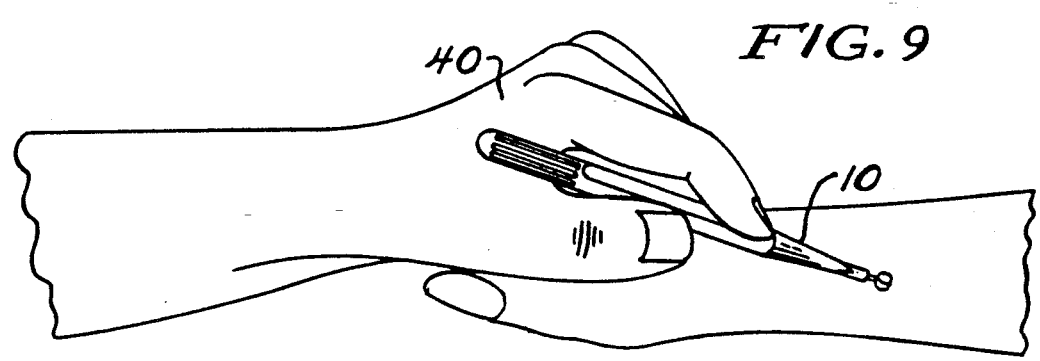

DISPOSABLE DERMAL CURETTE

This is a continuation of copending application Ser. No. 07/427,791, filed on Oct. 27, 1989 now abandoned.

BACKGROUND OF THE INVENTION

This invention relates generally to medical devices for scraping skin lesions, and more particularly to an improved disposable dermal curette which is responsive to the sensory-dependent nature of scraping procedures.

A dermal curette is a device used by medical practitioners for scraping growths, such as skin cancers, warts, actinic keratoses and seborrheic keratoses, from the surface of the skin. Generally, such devices are simple in construction, with a handle and a working element having a sharpened edge which is used to scrape the surface of the skin and remove the lesion. The working element is commonly a circular or ring-like configuration providing a curved or circular sharpened edge as the working surface of the curette.

There are generally three basic types of dermal curettes: the Fox Curette, the Piffard Curette and the eye curette. The Fox Curette is a device having a flat handle, usually metallic, with a generally cylindrical arm extending from the handle, also metallic, terminating in a working element having an oval or rounded-loop cutting edge. The Piffard Curette has a large metal handle tapering inwardly from the bottom of the handle, with a generally cylindrical metallic arm extending from the handle and terminating in a working element having an oval or rounded-loop cutting edge. The Piffard Curette is further provided with grooves or ribbed surfaces extending lengthwise along the handle of the curette. The eye curette is similar in design to the Fox Curette, but has a working element which is dish-like rather than looped-shaped, resulting in a working edge with a scooping action. The eye curette also has grooves or ribbed surfaces which extend around the width of the handle.

Variations of the dermal curettes described above are available and are identified and marketed as the Buck, Skeele or Heath curettes. These curettes, as well as the ones described above, are reusable, that is, designed and manufactured for repeated use after sterilization and, if necessary, resharpening.

Dermal curettes of such designs have been, and are currently being, used by physicians in medical procedures for the removal of lesions and unhealthy growths from the surface of the skin of a patient. Generally, in such procedures, the physician anesthetizes the area, removes the lesion with a scraping action utilizing a dermal curette and then cauterizes or electrode-siccates the area scraped. Sometimes the procedure is reversed in part and, after anesthetizing the area, the lesion is desiccated and then scraped using a curette. Ideally, only the lesions or unhealthy tissues or growths are removed in the scraping procedure with minimal destruction of the remaining healthy tissues.

As with many medical procedures, the effectiveness of such scraping procedures depends upon two interrelated factors, namely, the skill of the physician and the design of the tool used. Abnormalities of the skin, such as cancers, warts, actinic keratoses and seborrheic keratoses, differ to the touch from healthy tissues. Therefore, the experienced physician relies on the sense of touch during the scraping procedure and "feels" the difference between healthy and unhealthy tissues. With the proper tools, the physician can use his sense of touch to judge the depth of scraping necessary to remove only the unhealthy tissues, leaving the healthy tissues relatively unharmed.

In view of the sensory-dependent nature of such procedures, the design of the tool used is of critical importance. The curette must have a working element which is sharp enough to cut rather than pull and distort the tissue. Reusable curettes, like those described above, dull easily and do not hold a sharp edge very well. Thus, a curette which provides a working element of consistent sharpness, which the disposable curette of the present invention provides because of its one-time use, is needed. Furthermore, the curette should have a handle of sufficient weight to provide the balance necessary to allow the physician to properly "feel" the lesion, and an overall design which provides the physician with maximum control of the tool in use.

While the dermal curettes available have attempted to compensate for these factors, it has been determined that a need still exists for a dermal curette which is responsive to the sensory-dependent nature of such medical procedures. The present invention has been developed in response to that need, and provides an improved dermal curette having a working edge with consistent sharpness which is suitable for scraping procedures and a handle which is properly balanced and also designed to allow the user maximum control of the curette when used in such procedures.

SUMMARY OF THE INVENTION

It is an object of this invention to provide an improved dermal curette which can be utilized in scraping lesions and growths from the surface of a patient's skin.

It is another object of this invention to provide an improved dermal curette having a working edge of consistent sharpness which is capable of producing a scraping action when used in removing lesions from the surface of a patient's skin.

It is a further object of this invention to provide an improved dermal curette having the proper balance and design to allow the user maximum control in scraping lesions from the surface of a patient's skin so that the experienced physician need scrape only to the depth necessary, minimizing potentially disfiguring results of such scraping procedures.

The present invention relates to a disposable dermal curette designed to be used in scraping lesions and unhealthy tissues from the surface of a patient's skin. The curette includes a generally cylindrical plastic handle having a proximal end portion, a mid-section portion and a distal end portion with a generally circular or looped-shaped working element attached to the proximal end portion. For control and balance, the distal end portion of the handle is provided with a textured surface, preferably grooved or ribbed surfaces, extending lengthwise along the distal end portion; the proximal end portion also tapers inwardly to form a flat-nosed surface at its end for attachment of the working element. The mid-section portion of the handle is defined by a recessed flat surface extending lengthwise along the top of the mid-section portion; the remainder of the mid-section portion is generally cylindrical in shape. For maximum control and proper balance, the proximal end portion may further be provided with a textured surface similar to the distal end portion and the mid-section portion may further be provided with a finely textured surface extending around its width. Finally, the working element is provided with at least one cutting edge which is sharpened to a degree necessary to remove lesions from the skin of a patient by scraping.

DESCRIPTION OF THE INVENTION

In the figures:

FIG. 1 shows a side view of the dermal curette of the present invention;

FIG. 2 shows a top view of the dermal curette of the present invention;

FIG. 3 shows a bottom view of the dermal curette of the present invention;

FIG. 4 shows a front end view of the dermal curette of the present invention;

FIG. 5 shows a rear end view of the dermal curette of the present invention;

FIG. 6 is an illustration of the metal working element of the dermal curette of the present invention;

FIG. 7 is a sectional view of the metal working element of the dermal curette of the present invention taken through FIG. 6; and, FIGS. 8 and 9 show the dermal curette of the present invention held by a user in two of the many possible positions.

DETAILED DESCRIPTION OF THE INVENTION

Referring first to FIGS. 1 through 3, the dermal curette 10 of the present invention may be seen as a whole. The curette 10 includes a handle 12 and a working element 14. The handle 12 is generally cylindrical in shape and includes a proximal end portion 16, a mid-section portion 18 and a distal end portion 20. The proximal end portion 16 tapers inwardly from a point near the mid-section portion to point near the proximal end of the handle, and terminates in a generally flat-nosed end 22. In the preferred embodiment, the proximal end portion 16 may also be provided with a textured surface, preferably grooved or ribbed surfaces, such grooved or ribbed surfaces extending lengthwise from a point near the mid-section portion 18 to a point near the flat-nosed end 22 of the handle.

As also shown in FIGS. 1 through 3, the distal end portion 20 of handle 12 is generally cylindrical in shape and preferably terminates in a notched end 24, as shown in FIG. 5. The distal end portion is provided with a textured surface, preferably grooved or ribbed surfaces 26, which extend lengthwise from a point near the mid-section portion 18 to a point near its notched end 24. The grooves or ribbed surfaces 26 may, but need not, extend to the end of the distal end portion, or may extend to the edges of the notched end 24.

Located between the proximal end portion 16 and the distal end portion 20 is the mid-section portion 18. As shown in greater detail in FIG. 2, the mid-section portion 18 is provided with flattened surface 28 on the top of the handle, with the flattened surface 28 being recessed relative to the adjacent sections of the proximal end portion 16 and the distal end portion 20. Thus, the flattened surface 28 of the mid-section portion 18 lies below the adjacent sections of the proximal and distal end portions.

As further shown in FIGS. 1 and 3, the remainder of the mid-section portion 18 is generally cylindrical in shape. The mid-section portion 18 may be further provided with a textured surface, preferably finely grooved or ribbed surfaces extending around the width of its cylindrical surface. The textured surface, i.e., the finely grooved or ribbed surfaces on the mid-section portion 18, may also extend down through the crests of the grooved or ribbed surfaces 26 of the distal end portion 20 providing the distal end portion 20 with additional traction.

As shown generally in FIGS. 1 through 3, and more particularly in FIG. 4, the working element 14 is attached to the flat-nosed end portion 22 of the handle 12. The working element 14, shown in FIG. 6 without the handle, is generally circular or loop-shaped in design, and is provided with at least one cutting edge 30. The cutting edge 30, as shown in sectional view in FIG. 7, is provided by sharpening methods generally known to those skilled in the art and sharpened to a degree sufficient to allow the curette to be used in scraping lesions from the surface of a patient's skin. The cutting edge 30 is preferably sharp enough to scrape but not so sharp as to result in a scooping effect when the curette is used. If, however, a scooping effect is desired, then the cutting edge 30 of the working element 14 may be provided with a sharper surface. Also, both sides of the working element 14 may be sharpened to provide two cutting edges, one on either side of the working element 14.

As will be appreciated by those skilled in the art, the handle 12 of the dermal curette of the present invention is made from plastic materials which are suitable for injection molding processes, with high impact polystyrene being the preferred material. The handle is designed, and should be molded with the features described above, to provide a properly balanced curette which allows for maximum control in the hands of the physician. The textured surfaces of the proximal end portion, and optional textured surfaces of the mid-section and distal end portions, as well as the recessed surface of the mid-section, provide traction and gripping surfaces, and reduce the potential for slippage when the curette is actually used. Also, the material and design of the handle provide the user with a curette having the weight necessary to balance properly the curette, "feel" the lesion, and determine the depth of scraping necessary to remove the unhealthy tissues while leaving the healthy tissues intact.

As will also be appreciated by those skilled in the art, the working element 14 is basically metallic in composition, preferably stainless steel type 301. The working element is formed by press forming. The cutting edge is preferably single beveled, ground and honed. The degree of sharpness may be controlled by a single primary grind of 7° angle and the double honed angle of 32°. The preferable range of sharpness is ±4° for the single primary and ±5° for the double honed for use in scraping procedures.

The advantages of the dermal curette of the present invention may be more readily understood by reference to examples of its actual use. Referring to FIG. 8, the dermal curette 10 is shown as it is commonly held in the hand 40 of the user. The working element of the curette is a sharp to semi-sharp, round cutting instrument attached to a handle as described above. The handle is most commonly held firmly between the thumb and the second and third fingers, much as one would hold a writing instrument such as a pen or pencil. A second common holding position, as shown in FIG. 9, is to grasp the neck or mid-handle handle of the curette from above with the thumb and second and third fingers, with the tip of the handle steadied against the hypothenar area of the palm (much as one holds a kitchen knife when slicing a tomato or slicing meat in thin slices).

The physician chooses the holding position most suitable for his use, and after preparation of the area or areas to be scraped, takes the dermal curette in hand, as described above, and begins the scraping procedure. Using the first or second holding positions, one moves across and through the lesion to be removed with firm to hard pressure depending upon 1) the nature of the lesion, 2) the sharpness of the curette and 3) the desired depth required for removal of the growth. The scraping and cutting processes may be repeated multiple times until all of the tissue, benign or malignant, is removed. Once the procedure is completed, the used curette is disposed of; in this manner, the scraping procedure for each patient is performed with a new curette, providing the physician and patient with a scraping device with consistent sharpness.

It will be understood by those skilled in the art that, while this invention has been described with reference to a preferred embodiment, various changes may be made without departing from the scope of the invention. Therefore, it is intended that the invention not be limited to the particular embodiment disclosed as the best mode contemplated for carrying out this invention, but that the invention will include all embodiments falling within the scope of the claims set forth below.

What is claimed is:

1. A disposable dermal curette comprising:
   a generally cylindrical plastic handle having a proximal end portion, a distal end portion and a mid-section portion in between said end portions;
   the proximal end portion of the handle tapering inwardly from a point near the mid-section portion to a point near a flat-nosed end of the handle;
   the distal end portion being generally cylindrical in shape and having a textured surface extending substantially along its entire length;
   the mid-section portion having a flattened surface on the top side of the handle, with the flattened surface being recessed relative to the adjacent sections of the proximal end and distal end portions, the remainder of the mid-section portion being generally cylindrical in shape;
   said mid-section portion and recessed flattened surface being substantially centrally located on said handle between said proximal end and distal end portions and extending approximately one-half of the total length of said handle; and,
   a working element having a generally circular or loop-shaped cutting edge for scraping fixedly attached directly to the flat-nosed end of the proximal end of the handle, said cutting edge being disposed substantially adjacent to said flat-nosed end.

2. The dermal curette of claim 1, wherein the working element is provided with two cutting edges.

3. The dermal curette of claim 1, wherein the handle is composed of high impact polystyrene.

4. A disposable dermal curette comprising:
   a generally cylindrical plastic handle having a proximal end portion, a distal end portion and mid-section portion in between said end portions;
   the proximal end portion of the handle tapering inwardly from a point near the mid-section portion to a flat-nosed end of the handle and having a textured surface extending substantially the length of the proximal end portion;
   the distal end portion being generally cylindrical in shape and having a textured surface extending substantially along its entire length;
   the mid-section portion having a flattened surface on the top side of the handle, with the flattened surface being recessed relative to the adjacent sections of the proximal end and distal end portions, the remainder of the mid-section portion being generally cylindrical in shape and having a finely textured surface extending along its width;
   said mid-section portion and recessed flattened surface being substantially centrally located on said handle between said proximal end and distal end portions and extending approximately one-half of the total length of said handle; and,
   a working element having a generally circular or loop-shaped cutting edge for scraping fixedly attached directly to the flat-nosed end of the proximal end of the handle, said cutting edge being disposed substantially adjacent to said flat-nosed end.

5. The dermal curette of claim 4, wherein the textured surfaces of the proximal end and distal end portions are grooved or ribbed surfaces and the finely textured surface of the mid-section portion is a series of fine grooves or ribs extending along the width of the cylindrical surface of the mid-section portion.

6. The dermal curette of claim 5, wherein the fine grooves or ribs of the mid-section portion extend down along the crests of the grooves or ribs of the distal end portion.

7. The dermal curette of claim 4, wherein the working element is provided with two cutting edges.

8. The dermal curette of claim 4, wherein the handle is composed of high impact polystyrene.

* * * * *

UNITED STATES PATENT AND TRADEMARK OFFICE
CERTIFICATE OF CORRECTION

PATENT NO. : 5,116,346

DATED : May 26, 1992

INVENTOR(S) : Charles R. Yeh

It is certified that error appears in the above—identified patent and that said Letters Patent is hereby corrected as shown below:

On the title page of the patent, please add as the second inventor -- Dr. Joseph McGuire, 4251 Manuela Court, Palo Alto, California 94306 --.

Signed and Sealed this

Twelfth Day of October, 1993

Attest:

BRUCE LEHMAN

Attesting Officer

Commissioner of Patents and Trademarks